US00PP36610P2

(12) United States Plant Patent
Hansen

(10) Patent No.: US PP36,610 P2
(45) Date of Patent: Apr. 15, 2025

(54) ***HEUCHERA* PLANT NAMED 'Prom Dress'**

(50) Latin Name: ***Heuchera* hybrid**
Varietal Denomination: Prom Dress

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,302

(22) Filed: Oct. 22, 2024

(51) Int. Cl.
*A01H 5/12* (2018.01)
*A01H 6/80* (2018.01)

(52) U.S. Cl.
USPC ..... Plt./440

(58) Field of Classification Search
USPC ..... Plt./440
See application file for complete search history.

*Primary Examiner* — Susan McCormick Ewoldt

(57) ABSTRACT

The new and distinct hybrid of *Heuchera* plant named 'Prom Dress' has large, cordate, moderately-dissected, heavily-wavy leaf blades of purplish-charcoal with a pinkish-pewter overlay between the veins that becomes more pewter through the season. The new plant has upright, branched panicles producing airy pinkish flower effect. The new plant is vigorous and produces large clumps with many dense leaves and is useful in the landscape or in containers. The large-sized, cordate, leaf blades are moderately dissected at five main lobes;

2 Drawing Sheets

Botanical denomination: *Heuchera* hybrid.
Variety denomination: 'Prom Dress'.

STATEMENT REGARDING PRIOR DISCLOSURES UNDER 37 CFR 1.77(B)(6)

The first public introduction of *Heuchera* 'Prom Dress' was a brief description and photograph on Feb. 1, 2024, on a website maintained by Walters Gardens, Inc. Subsequently, on May 26, 2024, Walters Gardens, Inc. introduced the new plant in the "Walters Gardens 2024-2025 Catalog" with a brief description and photograph. The first offer for sale of the new plant was by Walters Gardens, Inc. to Edwards Greenhouse on Oct. 23, 2023. Walters Gardens, Inc. obtained the new plant and information about the new plant directly from the inventor. No plants of *Heuchera* 'Prom Dress' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of Coral Bells in the Saxifragaceae family and given the cultivar name of 'Prom Dress'. 'Prom Dress' was hybridized by the inventor on Jan. 2, 2017, in the greenhouses of a wholesale perennial nursery in Zeeland, Michigan, USA and assigned the breeder code 17-1-16. The seed or female parent was 'Peachberry Ice' U.S. Plant Pat. No. 31,433; the male parent was the proprietary, unreleased and unnamed hybrid assigned the breeder code 15-42-3 (not patented).

*Heuchera* 'Prom Dress' was first selected in the fall of 2019 and passed final evaluation in the fall of 2020 from among thousands of other seedlings from the same cross and other crosses. 'Prom Dress' has been asexually propagated by basal shoot cuttings at the same nursery in Zeeland, MI in 2019 and by careful shoot tip tissue culture propagation, and the resultant plants have remained stable and continued to exhibit the same characteristics as the original plant for multiple generations.

BRIEF SUMMARY OF THE INVENTION

*Heuchera* 'Prom Dress' differs from its parents as well as all other coral bells known to the applicant in the following combined traits:

1. The large-sized, cordate, leaf blades are moderately dissected at five main lobes;
2. Leaves have heavily wavy margins easily showing the underside;
3. Foliage has lightly overlapping and indented or folded at major veins;
4. Leaves are deep purplish-charcoal with a pinkish-pewter overlay between the veins that develops to a more pewter.
5. Produces large-sized clumps and many individual leaves.
6. Plant habit is vigorous with medium height stems of airy pinkish flowers.

In comparison to the new plant, the female parent has leaves that are more peachy-orange, less wavy margins, and not as dark purple with pinkish pewter, and the flowers are more cream-colored on darker wine-color panicles. The male parent is similar in habit and size but the leaves are flatter and less ruffled, and more purplish and less pewter between the veins.

The most similar cultivars known to the inventor are: 'Bella Notte' U.S. Plant Pat. No. 24,291, 'Black Beauty' U.S. Plant Pat. No. 13,288, 'Black Pearl' U.S. Plant Pat. No. 29,395, 'Black Knight' 'Black Taffeta' U.S. Plant Pat. No. 26,162 'Evening Gown' U.S. Plant Pat. No. 34,288, 'Obsidian' U.S. Plant Pat. No. 14,836, 'Timeless Night' U.S. Plant Pat. No. 32,134, 'Timeless Treasure' U.S. Plant Pat. No. 31,987, and 'Wildberry' U.S. Plant Pat. No. 31,222.

'Bella Notte' has larger flowers on shorter panicles, smaller flatter leaves with no ruffling of the foliage, the top surface is not as shiny, the coloration is more magenta with a reduced silvery upper surface. 'Black Beauty' has a smaller habit and smaller leaves and the foliage color tends to be a lighter reddish-purple. 'Black Pearl' has larger leaves with less cupping, less wavy margins, and without silver or pewter between the veins. 'Black Taffeta' has smaller leaves with more incised margins and the flowers are cream-colored. 'Obsidian' has smaller habit, smaller and flatter foliage with shallower incisions between the lobes, and the flowers are creamy-white. 'Timeless Night' has a similar habit with flatter foliage that less dissected between the lobes, the leaves are purplish-black without pewter or silver between the veins, and it flowers more profusely on shorter panicles. 'Timeless Treasure' has smaller leaves and larger darker reddish flowers on shorter panicles over a longer season. 'Wildberry' has foliage that is smaller, flatter, less dissected, more glossy, and has a more purplish in color.

BRIEF DESCRIPTION OF THE DRAWINGS

The photographs of the new plant demonstrates the overall appearance of *Heuchera* 'Prom Dress' including the unique traits. The colors are as accurate as reasonably possible with modern color reproductions. Some slight variation of color may occur as a result of lighting quality, intensity, wavelength, and direction or reflection.

DETAILED BOTANICAL DESCRIPTION

Figure 1:
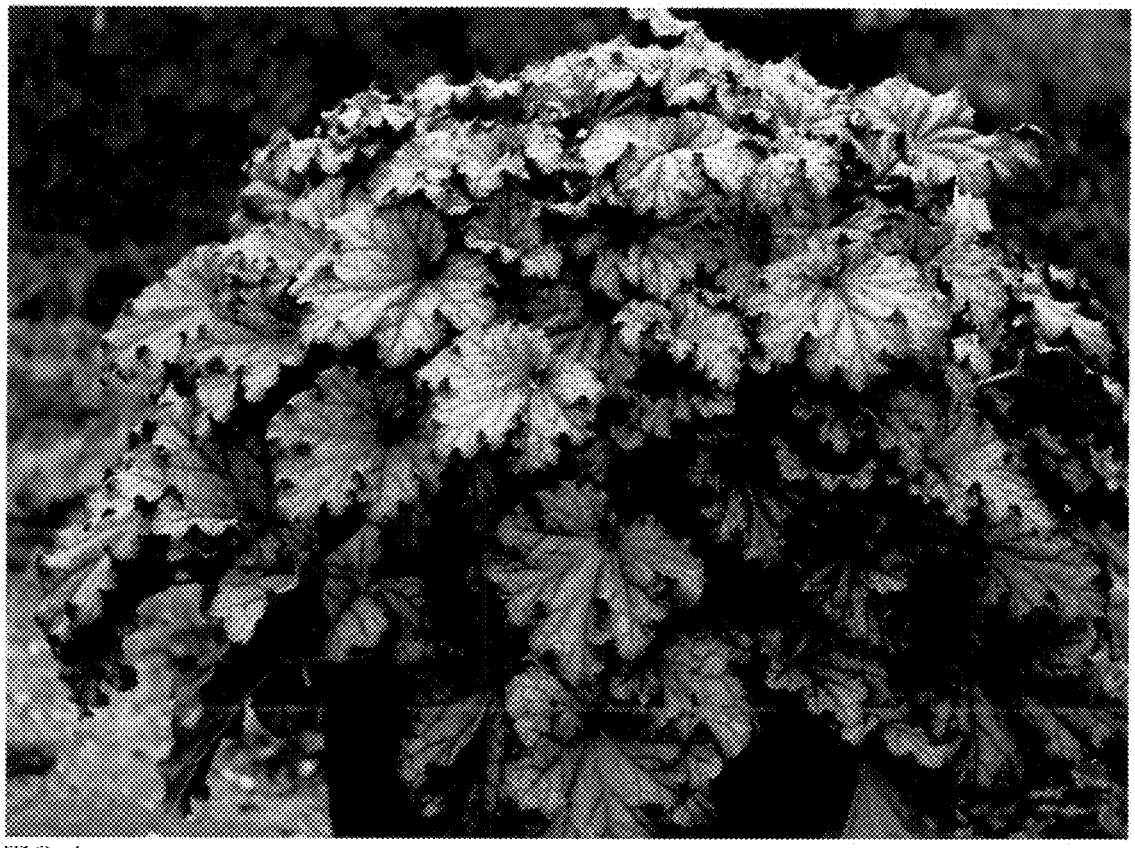
FIG. 1 shows a two-year-old plant late in the season.
Figure 2:
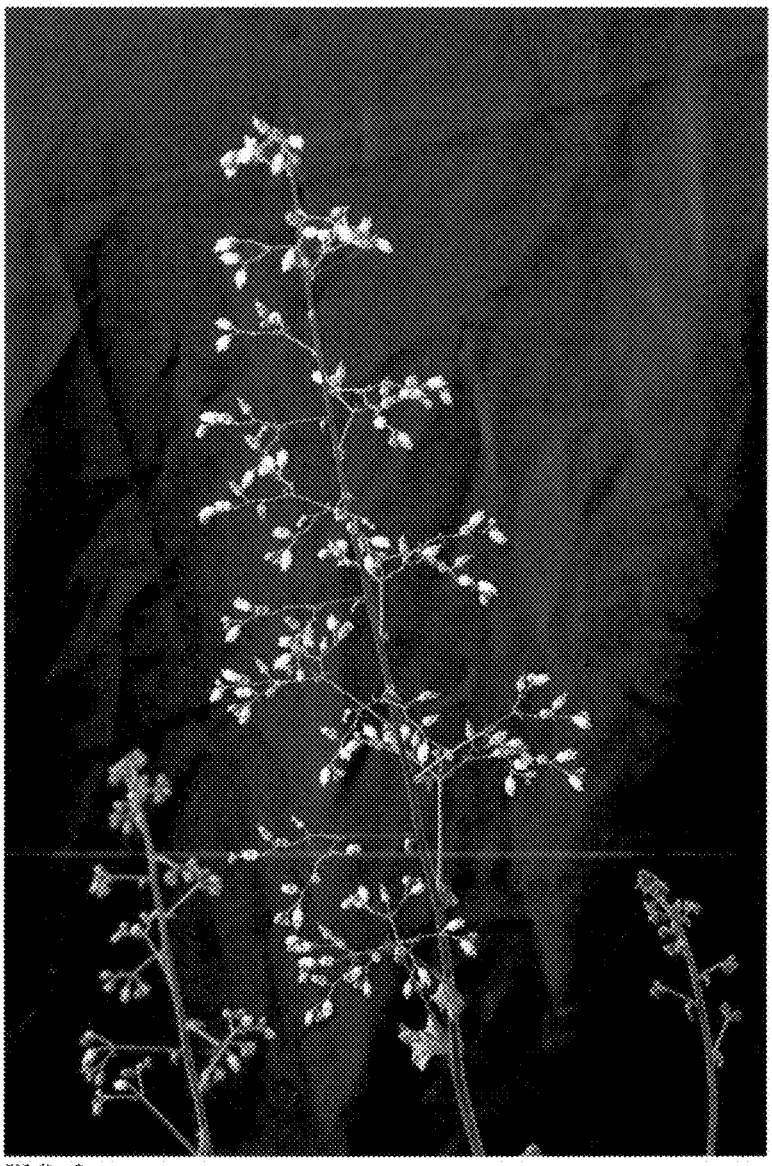
FIG. 2 shows the scapes with flowers and buds.

The following description is based on a two-year-old plant growing in a lightly shaded greenhouse and one-year-old plants in an outdoor partially shaded display garden in Zeeland, Michigan, USA. The new plant has not been grown under all possible environments and may phenotypically appear different under different conditions such as light, temperatures, fertilizer, and water, without any difference in genotype. The color descriptions used are from the 2015 edition of The Royal Horticultural Society Colour Chart except where common dictionary terms are used.

Parentage: Female or seed parent was 'Peachberry Ice', and the male or pollen parent was 15-42-3;

Plant habit: Hardy herbaceous perennial with basal rosette of foliage; mounded foliage about 24 cm tall and 52 cm in diameter with scapes to about 38 cm tall; stems to about 4 cm long and 2.5 cm diameter at base completely covered with petiole stipules, with about 40 leaves per stem and one main stem per plant;

Roots: Fibrous, finely branched; nearest RHS NN155B depending on soil type;

Growth rate: Vigorous, rapid; rooting from cutting in two weeks and finishing in a 3.8-liter container in about 16 weeks from a 25 mm plug;

Foliage: Cordate; moderately penta-lobed (dissected about 35 mm deep), with basal lobes extending 20 mm beyond petiole and frequently imbricate to 10 mm; cupped to 20 mm deep centered around petiole and apex slightly reflex; apex and major and minor lobe apices rounded and apiculate; base cordate; margin crenate and micro-ciliolate; bullate in the leaf center on young leaves; plicate around primary veins; adaxial and abaxial surfaces sparsely micro-puberulent, adaxial slightly lustrous becoming matte and abaxial moderately lustrous; high number of leaf indentations with four major indentations and about 40 to 60 smaller indentations; leaf margin undulation moderately strong; moderately to strongly.

Leaf blade size: To about 14.5 cm wide and 14.5 cm long, average about 13.5 cm wide and 13.5 cm long;

Leaf color: Seasonally variable; initial spring and expanding adaxial between RHS 187B and RHS N186C, initial spring and expanding abaxial nearest RHS 187B; fully expanded adaxial leaves near flowering nearest RHS N187B with a slight blush of nearest RHS 186B between veins area surrounding veins nearest RHS N187A, fully expanded abaxial leaves near flowering abaxial leaves nearest RHS N79A; late season fall adaxial between RHS N187C and RHS 197B with region surrounding veins between RHS N186A and RHS N189A, late season fall abaxial variable, between RHS N79B and RHS N77B;

Veins: Palmate; sparsely hirsutulous adaxial and hirsutulous abaxial; costate abaxial and slightly concave adaxial;

Vein color: Emerging or initial spring adaxial nearest RHS 182B, emerging or early spring abaxial nearest RHS 187B; near flowering adaxial primary veins nearest RHS N187B and secondary veins nearest RHS N187A, near flowering season abaxial proximal main veins between RHS N77B and RHS N77C and distally and secondary veins nearest RHS N77A; late season fall adaxial proximally nearest RHS 176A and distally between RHS 177A and RHS 187A; late season fall abaxial proximal between RHS 182D and RHS 155A; late season adaxial proximal main veins between RHS N186B and RHS 182C and distally and secondary veins nearest RHS N186A;

Petiole: Cylindrical; base amplexicaul; stiff; outer leaves outwardly and inner leaves slightly arcuate upwardly; hirsute with hairs to about 2 mm long; to about 20 cm long, 5 mm across at base above stipule, and 3 mm across below petiole, average about 17 cm long, 4.5 mm across above stipule and 2.5 mm across below petiole;

Petiole color: Varying with season; young emerging and near flowering season nearest RHS N186C; late season fall adaxial nearest RHS 186B and abaxial nearest RHS 183D;

Stipule: At base of petiole; adaxial and abaxial glabrous; margin ciliate; to about 30 mm long and about 17 cm wide at base and 7 mm wide at apex, with two distally-flared acute lobes about 7 mm long;

Stipule color: Adaxial and abaxial variable, nearest RHS N79B, nearest RHS 71B and nearest RHS 187A;

Peduncle: Panicle; cylindrical; stiff; pubescent; upright; to about 70 cm long and 5 mm diameter at base, average about 62 cm tall and about 4 mm diameter; about seven per plant; with about 200 flowers per panicle;

Peduncle color: Nearest RHS 187A; branches nearest RHS 187A;

Inflorescence: Compound-branched panicle with up to 24 branches to about 6 cm long and about 1 mm diameter at base, decreasing in size distally; branches upwardly; flower density is dense; flowering in upper 46 cm and 10 cm wide;

Flowering longevity: Panicle effective for about three weeks;

Flower density: Moderately open;

Pedicel: Cylindrical; finely puberulent, to about 3 mm long and 0.5 mm diameter;

Pedicel color: Between RHS 187A and RHS N186B;

Buds one day prior to opening: Oblong ellipsoidal; acute apex and attenuate base; puberulent; about 4 mm long and 2 mm diameter near middle;

Bud color one day prior to opening: Proximal portion between RHS 183C and RHS 182B, distally nearest RHS 71A;

Flower: Perfect, campanulate, actinomorphic, about 6 mm long to exserted style and 4 mm in diameter at face; corolla to 5 mm long and 4 mm diameter; individual flowers lasting about 4 days on plant or as cut flower; rarely persistent;

Flower attitude: Outwardly to slightly upwardly;

Calyx: Five sepals; apex acute; about 5 mm long and 4 mm wide, base fused in proximal 3.5 mm to form hypanthium;

Sepals: Five; glabrous adaxial; puberulent to glandular abaxial; rarely persistent;

Calyx color: Adaxial nearest RHS 182D with apex nearest RHS 138C, abaxial base between RHS 177D and RHS 182D and distally between RHS 186B and RHS 187D;

Petals: Five, linear to oblanceolate, acute apex and attenuate base; margin entire; glabrous abaxial and puberulent adaxial; adnate to adaxial sepals in proximal 0.5 mm; about 3 mm long and 0.5 mm wide near middle;

Petal color: Abaxial and adaxial nearest RHS NN155D;

Androecium: Five;

*Filaments*.—Five; glabrous; adnate to adaxial calyx about 1 mm above base; thin, glabrous; about 2.5 mm long and about 0.2 mm diameter; color nearest RHS NN155D.

*Anthers*.—Ellipsoidal, distinct, basifixed, longitudinal; about 0.5 mm long; color nearest RHS 25B.

*Pollen*.—Abundant; color nearest RHS 12B.

Gynoecium: One, two-beaked; half-inferior; 6 mm long;

*Style*.—Bifid; exserted; split apart at apex of ovary; about 4 mm long and about 0.5 mm diameter; color nearest RHS NN155C.

*Stigma*.—Acute apex, about 0.5 mm diameter; color nearest RHS 155A with a slight blush of nearest RHS 185C.

*Ovary*.—Half-inferior, about 1.5 mm long and 1.5 mm diameter; ellipsoidal to globose; apex acute, base rounded; color nearest RHS 145C.

Fruit and seed: Not yet observed;

Growth: 'Prom Dress' grows best with ample moisture and drainage in either sun or shade. Cold hardy from USDA zones 4 to 9.

Disease and pest tolerance: Resistance and tolerance outside of that normal for *Heuchera* is not known.

It is claimed:

1. The new and distinct *Heuchera* plant named 'Prom Dress' as herein described and illustrated.

* * * * *